United States Patent [19]
Babcock et al.

[11] 4,013,688
[45] Mar. 22, 1977

[54] RADIOIMMUNOASSAY AGENTS

[75] Inventors: John C. Babcock; J. Allan Campbell, both of Kalamazoo, Mich.

[73] Assignee: The Upjohn Company, Kalamazoo, Mich.

[22] Filed: Dec. 20, 1972

[21] Appl. No.: 316,974

[52] U.S. Cl. .................. 260/397.45; 260/397.5; 260/239.5

[51] Int. Cl.² .......................................... C07J 5/00

[58] Field of Search ...... Machine Searched Steroids

[56] References Cited

UNITED STATES PATENTS

| | | | |
|---|---|---|---|
| 2,666,070 | 1/1954 | Murray et al. | 260/397.4 |
| 2,698,331 | 12/1954 | Murray et al. | 260/397.45 |
| 3,055,921 | 9/1962 | Clinton | 260/397.45 |
| 3,086,033 | 4/1963 | Irmscher et al. | 260/397.45 |
| 3,178,457 | 4/1965 | deStevens | 260/397.4 |
| 3,225,034 | 12/1965 | Hewett et al. | 260/239.5 |
| 3,462,423 | 8/1969 | Consonni et al. | 260/239.55 |

*Primary Examiner*—Elbert L. Roberts
*Attorney, Agent, or Firm*—Willard L. Cheesman; Martin B. Barancik

[57] ABSTRACT

Novel steroid derivatives containing a tyrosine ester amide group linked to an 11-hydroxysteroid alkylene dicarboxylic hemi-ester are described, suitable for iodination with radioactive iodine, useful in radioimmunoassay.

1 Claim, No Drawings

RADIOIMMUNOASSAY AGENTS

BACKGROUND OF THE INVENTION

It is known that when 11α-hydroxy progesterone acid succinate was attached to a protein molecule such as bovine serum albumin (BSA) and administered to an animal, antibodies of high titre very specific to progesterone were produced. This was regarded in the art as a significant breakthrough in steroid immunoassay methodology. The 11α-hydroxy position in the steroid molecule is remote from the important biological centers of the molecule and generally provides a means for attachment by means of a succinate bridge to protein-like substances, thus to form steriod conjugates which, when administered to animals induce formation of antibodies generally useful in the aforesaid radioimmunoassays. The development of a radioimmunoassay procedure for general steroid determination can be accomplished through antibodies to a steroid hemi-ester protein conjugate wherein the hemi-ester is suitably the hemi-succinate, preferably linked through an ester linkage to the steroid molecule at a position in the molecule that is remote from the biologically functional groups that are the key to the desired discrimination. For example, such a position should be remote from the steroid ring A and D functionality of the sex hormone type of steroid, and from the combination of ring A and D functionality in adrenocortical hormones.

In practice conjugation to the protein is commonly through remote amine functions of protein amino acids, and the number of protein residues is preferably between 10 and 40 per protein molecule. In the past the antibodies produced, commonly after subcutaneous or intradermal administration of the conjugate in Freund's adjuvant to the antibodies-donor, were used in a binding assay using in the conjugate a labeled steroid chosen so as to compete with the steroid to be assayed. The steroids, those that were bound by the antibody and those that were not bound, were separated, commonly by centrifugation after immune precipitation, or by charcoal adsorption, or by filtration when the antibody was chemically bound to discrete particles. The label associated with one or both fractions was counted, and the amount of steroid being assayed was calculated using standard calibrated curves.

This prior method ordinarily required a labeled steroid in the conjugate that corresponded to each steroid that was being assayed.

Because the preparation of individual labeled steroids is difficult and costly, often requiring multi-step syntheses using labeled starting materials, a need has rapidly developed for a simpler, less costly method for associating radioactivity with the steroid to be assayed.

It is known that the tyrosine methyl ester amides of certain steroid hemisuccinates could be radioiodinated and could serve then as the label-bearing steroid in a radioimmunoassay procedure. The steroid hemisuccinates were at $C_{17}$ in testosterone, at $C_{21}$ in aldosterone, corticosterone, cortisone, and deosycorticosterone, and at $C_3$ in Pregnenolone and estradiol (Niswender and Midgley in Piron and Caldwell "Immunologic Methods in Steroid Determination," Appleton-Century-Crofts, 1970, p. 149). Steroid hemisuccinates were conjugated to tyrosine methylester using the method of Oliver et al., J. Clin. Invest. 47, 1035, 1042 (1968) and were radioiodinated by the method of Niswender et al., Endocrinol. 84, 1166 (1969).

BRIEF SUMMARY OF THE INVENTION

The invention relates to novel steroid derivatives containing a tyrosine ester amide linked to an 11-hydroxy steroid alkylene dicarboxylic hemi-ester. These novel compounds are suitable for iodination with radioactive iodine. The novel compounds have the following structural formula

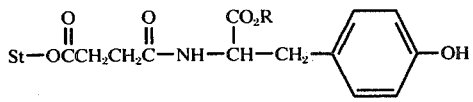

wherein St is a steroid moiety linked through the 11-carbon atom and corresponding to the steroid intended for assay, and R is a lower alkyl radical of from 1 to 6 carbon atoms. The $-CH_2CH_2-$ moiety can vary from 1 to 6 carbon atoms as in glutaric or other hydrocarbon alkyl dicarboxylic acid residues with 1 to 6 carbon atoms in the alkylene chain.

From the general formula above it can be seen that the St moiety is substituted at $C_{11}$ by a hydroxyl group which is functionalized as the 11-hemisuccinyl or other dicarboxyl ester; it can also be seen that the remote carboxyl group is further functionalized by an amide linkage with the amine group of the tyrosine moiety. The tyrosine ester fragment may be d-, l- or d,l-.

The steroid moiety is attached through the 11-position and is selected from those moieties listed below. Prior to esterification, the corresponding moieties are substituted by an 11-hydroxyl group. The isomeric orientation of the linkage with respect to the steroid 11-hydroxyl group is α when a methyl group is attached to the steroid $C_{10}$, and it is either α or β when a methyl group is not attached to $C_{10}$ as occurs in the 19-nor and the ring A aromatic moiety.

20α-hydroxypregn-4-en-3-one
20β-hydroxypregn-4-en-3-one
17α-hydroxypregn-4-ene-3,20-dione
21-hydroxypregn-4-ene-3,20-dione
17α,21-dihydroxypregn-4-ene-3,20-dione
17β-hydroxyandrost-4-en-3-one (testosterone)
17β-hydroxy-5α-androstan-3-one
17β-hydroxy-5β-androstan-3-one
5α-androstane-3β,17β-diol
17β-hydroxyester-4-en-3-one (19-nortestosterone)
estrone
estradiol
estriol
estr-5-ene-3β,17β-diol
androst-5-ene-3β,17β-diol
dehydroepiandrosterone
pregnenolone
21-hydroxypregnenolone
17α-hydroxypregnenolone
17,21-dihydroxypregnenolone The above novel compounds possess high affinity for antibodies obtained from laboratory and domesticated animals by administration of the conjugate of the 11-hydroxy steroid hemisuccinate or other dicarboxyl ester with foreign proteins such as bovine serum albumin, and thus afford high specificity and high sensitivity in the radioimmunoassay.

In addition to their high specificity and sensitivity the novel compounds of this invention are far more available and easier to make than $^3$H or $^{14}$C-labeled steroids of the prior art and are suitable for use in practical, accurate, and economical laboratory procedures. They have the additional advantage over $^3$H or $^{14}$C materials in that they are stable in their non-iodinated form and can be stored without extensive precaution until ready for use, whereon they can be radio-iodinated as needed.

Embraced within the scope of this invention are likewise certain novel steroid 11-hemisuccinates and other dicarboxylates useful in making the compounds of the formula above. In general these esters, e.g., the hemisuccinates, can be prepared by reacting the 11-hydroxy steroid compound with an esterifying agent, e.g., a succinoylating agent such as succinic anhydride in the presence of pyridine.

In the following description, the succinoyl compounds will be described by way of exemplification. In most instances the steroid to be esterified, e.g., succinoylated, hereafter referred to as the starting steroid, possesses one or more additional esterifiable hydroxyl groups, as for example the 17$\beta$-hydroxy group. The succinoylated steroid of this invention can be prepared in such cases by first making the disuccinate, usually by simply employing an excess of the succinic anhydride needed to make the bis acid succinate, and then partially and selectively hydrolyzing with sodium hydroxide. The partial hydrolysis can be carried out by reacting the bis acid succinate with an aqueous solution of sodium hydroxide under such conditions as to achieve progressive hydrolysis which can be followed by known analytic methods. This procedure is applicable to dihydroxylated and also to trihydroxylated steroids. When a tertiary hydroxyl group is present, however, it is ordinarily unreactive and does not undergo the succinoylation reaction.

The conjugates with tyrosine methyl ester corresponding to the formula above are prepared by reacting the 11-hydroxy steroid acid succinate with tyrosine lower alkyl ester in the presence of an amide forming agent such as carbonyldiimidazole under anhydrous conditions, 1-ethyl-3(3-dimethylaminopropyl)carbodiimide hydrochloride in partly aqueous solvents.

The novel intermediates, useful in making the radioimmunoassay agents of this invention, have the following general structural formula:

wherein St is a steroid moiety linked through the 11-carbon atom and corresponding to the steroid intended for assay and X is hydrogen or a cation such as an alkali metal ion or ammonia. The —CH$_2$CH$_2$— moiety can be represented generally by —R$_2$—, an alkylene chain having from 1 to 6 carbon atoms. Examples of steroid moieties are those corresponding to the steroids listed above, and the isomeric orientation of the linkage with respect to the steroid 11-hydroxyl group is $\alpha$ when a methyl group is attached to the steroid C$_{10}$, and it is either $\alpha$ or $\beta$ when a methyl group is not attached to C$_{10}$ as occurs in the 19-nor and the ring A aromatic moiety.

DETAILED DESCRIPTION

EXAMPLE 1

Preparation of 11-acid succinates where selectivity is not necessary.

(11$\alpha$-hydroxypregn-4-ene-3,20-dione 11-acid succinate)

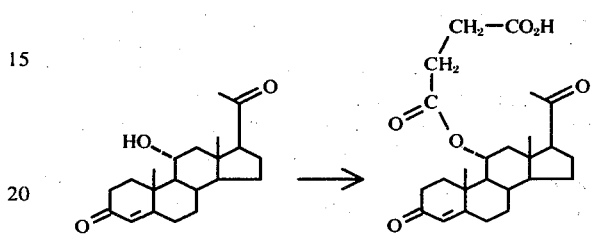

A solution of 10 g. of 11$\alpha$-hydroxyprogesterone, 15 g. of succinic anhydride in 100 ml. of pyridine was purged with N$_2$ and refluxed above 20 hours. The solution was poured into iced hydrochloric acid and the precipitate was extracted with ethyl acetate. The ethyl acetate solution was washed twice with water and extracted twice with aqueous sodium bicarbonate. (The product is now in the aqueous phase as the sodium salt.) The bicarbonate phases were washed with ethyl acetate and then combined and neutralized by dropwise addition of 6N hydrochloric acid. The newly formed acid succinate was extracted twice with ethyl acetate and washed with water until neutral, dried over sodium sulfate and concentrated to dryness. (Note: This extraction-purification procedure will be referred to in subsequent processes as the usual acid succinate extraction procedure.)

The residue was recrystallized twice from acetone-ether with charcoal treatments to give 4.5 g. of the acid succinate, m.p. 154°–159°, $\lambda$max$^{alc}$239 nm, $\epsilon$ = 16,150. Nmr: (C, Cl$_3$) $\delta$ 0.72 (S, C-18), 1.25 (S,D-19), 2.09 (S,C-21), 2.51 (S CO$_2$H—CH$_2$—CH$_2$—CO$_2$), 5.25 (m, C-11), 5.76 (S,C-4).

Anal. Calcd. for C$_{25}$H$_{34}$O$_6$: C, 69.74; H, 7.96. Found: C, 70.03; H, 7.81.

In like manner, other 11$\alpha$-mono hydroxy steroids such as 11$\alpha$-hydroxy androst-4-en-3,27-dione, afford the corresponding 11-acid succinate.

In like manner, other 11$\alpha$-hydroxy steroids containing additional unreactive hydroxyl substituents such as a tertiary hydroxyl substituent at C-17, for example, 11$\alpha$,17$\alpha$-dihyroxy-progesterone, 11$\alpha$,17$\beta$-dihydroxy-17-methyltestosterone and the corresponding 19-nor analogs, afford the corresponding 11-mono acid succinate.

Thus, following this procedure 11$\alpha$-hydroxy-androst-4-ene-3,27-dione 11 acid succinate and 11$\alpha$,17$\alpha$-dihydroxypregn-4-ene-3,20-dione 11 acid succinate were prepared.

EXAMPLE 2

Preparation of 11-succinates where poly-acid succinates form and selective hydrolysis removes all acid succinates except 11-succinates.

(11α,17β-dihydroxyandrost-4-en-3-one 11-acid succinate)

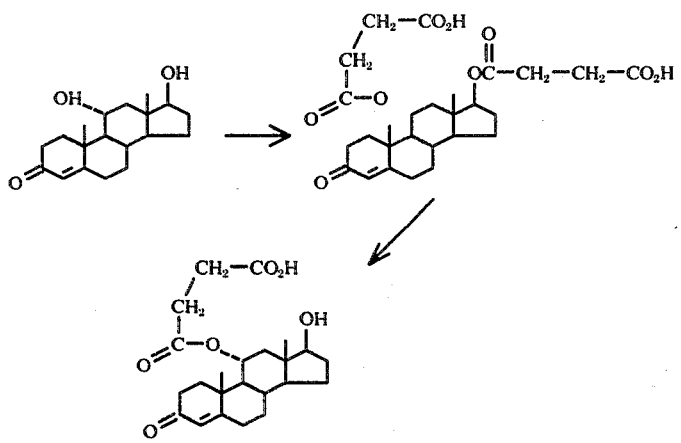

A mixture of 4 g. of 11α-hydroxytestosterone and 6 g. of succinic anhydride in 50 ml. of pyridine was heated at reflux under $N_2$ for 20 hours. After pouring into 80 ml. of conc. hydrochloric acid-ice the bis acid succinate was worked up by the usual acid succinate extraction procedure. Titration with 0.1N sodium hydroxide indicates two succinate groups per steroid molecule.

One gram of the bis acid succinate was dissolved in 9 ml. of 1.0N sodium hydroxide and diluted immediately to 100 ml. with water and with 6N hydrochloric acid and worked up by the usual acid succinate extraction procedure. For gas-liquid chromatographic (GLC) and thin layer chromatographic (TLC) analysis it was converted to the methyl ester with diazomethane.

This product was combined with material from a similar 3.4 g. run and recrystallized twice from acetone with charcoal treatment to give 1.1 g. of 11-acid succinate m.p. 200°–209°. λmax.$^{alc}$240 nm $\epsilon$=15,800; M.S. M+ 404, IR shows the expected bands, nmr (DMSO-D6); δ 0.73 (S, C-18), 1.10 (S, C-19) 2.48

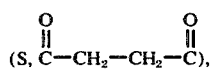

3.52 (M, C-17), 5.13 (S, C-11), 5.65 (S, C-4).

This procedure is applicable with dihydroxylated and trihydroxylated steroids when selectivity cannot be obtained in introduction of the succinate groups. When 11α-hydroxytestosterone in the above procedure is substituted by 11α,17β-dihydroxy-5α and 5β androstan-3-one, 3β,11α-dihydroxyandrost-5-en-17-one, 11α-hydroxypregnenolone, 11α,21-dihydroxypregn-4-en-3-one, 11α,17β-dihydroxy-19-nortestosterone 11α,17'-21-trihydroxyprogesterone 11α and 11α-hydroxy estradiol, 11α,17α-dihydroxypregnenolone, the corresponding 11α succinates are produced.

Using this method, 11α acid succinates of pregnenolone and 17β-hydroxy-5α-androstan-3-one were prepared.

EXAMPLE 3

Preparation of 11-succinates containing a phenolic A ring.

(3,11β-dihydroxyestra 1,3,5(10)-triene-17-one 11-acid succinate)

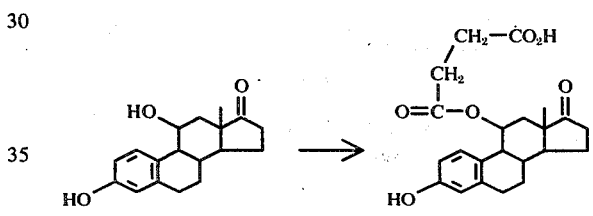

A solution of 1.0 g. of 11β-hydroxyestrone, 2 g. of succinic anhydride and 15 ml. of pyridine was heated under $N_2$ at reflux for 2 days. Thin-layer chromatography showed still a trace of starting material plus three slower moving spots. The reaction was poured into ice-hydrochloric acid. Purification by the usual acid succinate extraction procedure gave an amorphous solid, 1.0 g. It was a mixture by TLC analysis and consisted of 11-mono and 3,11-bis acid succinates. To obtain the monosuccinate the crude product was dissolved in 50 ml. of water containing 10 g. of potassium carbonate. The solution was purged with $N_2$ and stored at room temperature (R.T.) for 16 hours. It was worked up by the usual acid succinate extraction procedure to give a dark partly crystalline residue.

The crude 11-acid succinate was dissolved in about 25 ml. of acetone and poured on a 70 g. column of dry silica gel. The column was washed with 200 ml. of acetone containing 2% acetic acid. The product and a small portion of the color came off in the first 100 ml. wash. After removal of the solvent, the product was recrystallized from acetone-ethyl acetate to give 0.5 g. of off-white crystals, m.p. 168°–172°; i.r. 3340 (OH), 2660, 2570 (acid OH) 1725 (C=O); mnr (dimethylsulfoxide (DMSO)-D-6) δ 0.92 (S, C-18), 2.28

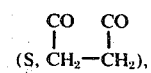

5.69 (S, C-11), 6.5 (Several bands, aromatic A ring), (this particular sample was solvated with ethyl acetate).

Anal. Calcd. for $C_{22}H_{36}O_6$: C, 68.38; H, 6.78. C, 68.42, H, 6.80.

This procedure is useful for selectively hydrolyzing acid succinate esters of phenolic hydroxyls and having other acid succinates unchanged.

EXAMPLE 4 estra-1,3,5(10)-triene-3,11β,17β-triol 11-acid succinate

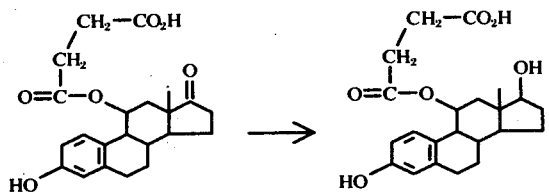

A solution of 0.37 g. of 11β-hydroxyestrone 11-hemisuccinate was dissolved in 10 ml. of saturated aqueous sodium bicarbonate and cooled in an ice bath and 50 mg. of sodium borohydride was added. After a few minutes, thin-layer chromatography (silica gel plate developed with 45—55—10 ethyl acetate-cyclohexane-acetic acid) showed no starting material remaining. The reaction mixture was acidified and worked up by the usual acid succinate extraction procedure. The crude residue was triturated with acetone and recrystallized from tetrahydrofuran-water-acetone, yield 0.3 g., m.p. 160°–184°, M.S. M+ 388 with trace ion impurity at 402, nmr. (DMSO-C-6) δ 0.87 (S-C-18) 2.05 (S, OC-CH₂-CH₂-CO) 3.51 (broad C-17), 5.60 (broad C-11), 6.5 (Several bands, aromatic A ring).

This reduction procedure is useful for the preparation of the 11α-acid succinates of 11α-hydroxy analogs of dehydroepiandrosterone, pregnenolone, progesterone, 3β-hydroxy-estr-5-en-17-one, and 5α-androstane-3,17-dione to 11α-hydroxy succinate derivatives of androst-5-ene-3β,17β-diol, pregn-5-ene-3β,20α and 20β diols, pregn-4-ene-3,20α and 20β diols, estr-5-en-3β,17β-diol and 5α-androstane-3β,17β-diol.

EXAMPLE 5

Preparation of 3β-hydroxy-Δ⁵-steroids via 3α,5α-cyclo-6β,11α-bis acid succinates.
(3β,11α-dihydroxypregn-5-en-20-one 11-acid succinate)

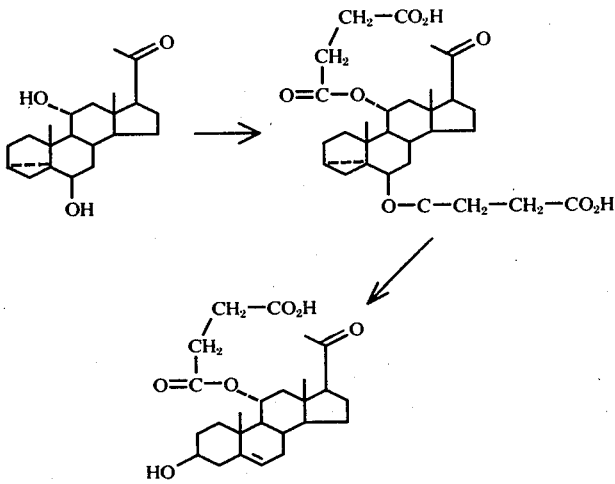

A solution of 4.0 g. of 6β,11α-dihydroxy-3α,5α-cyclopregnan-20-one, 6.0 g. of succinic anhydride in 40 ml. of pyridine was refluxed under N₂ for 20 hours. It was worked up by the usual acid succinate extraction procedure. The dark brown amorphous residue of 6,11-bis acid succinate was dissolved in ethyl acetate and treated with charcoal to remove some of the color. After removal of the solvent, the residue (4 g.) was dissolved in 150 ml. of acetone and 7.5 ml. of 1.0N perchloric acid was added. After 20 hours about 100 ml. of water was added and the acetone was evaporated on a rotary evaporator. The product was purified by the usual acid succinate extraction procedure and recrystallized three times from acetone-water then from methylene chloride-ether, m.p. 157°–164°, i.r. 3370 (OH), 2540 (acid OH) 1730, 1695 (C=O). nmr (CDCl₃) δ.71 (S, C-18), 1.11 (S, C-19) 2.15 (S, C-21), 2.69

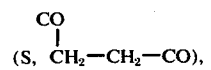

(S, CH₂—CH₂—CO), 3.55 (m, C-3), 5.43 (m, C-11) 5.55 (d, C-6) 6.60 (S, OH, erased with D₂O).

Anal. Calcd. for $C_{25}H_{36}O_6$: C, 69.42; H, 8.39. Found: C, 69.34; H, 8.44.

This reaction sequence is particularly useful since many i-steroids can be bioconverted to thier 11α-hydroxy analogues (See Wechter and Murray, J. Org. Chem. 28, 755 [1963]).

Thus, following the above procedure, one can substitute for 6β,11α-dihydroxy-3α,5α-cyclopregnan-20-one the following starting materials: 6β,11α,17α-trihydroxy-3α,5α-cyclopregnan-20-one, 6β,11α-dihydroxy-3α,5α-cycloandrostan-17-one, 17-methyl-3α,5α-cycloandrostan-6β,11α,17β-triol and the like to obtain the corresponding 3β-hydroxy-Δ⁵-steroid 11α-monohemisuccinates.

EXAMPLE 6

11α-hydroxyandrost-4-en-3,17-dione 11-acid succinate

A solution of 3.8 g. of 11α-hydroxyandrostenedione, 4 g. of succinic anhydride in 50 ml. of pyridine was heated at reflux under a $N_2$ atmosphere for 24 hours. The reaction mixture was black. It was poured into 50 ml. of iced 12 N hydrochloric acid. The gummy product was extracted with 1–1 ether-ethyl acetate and washed with water. The product, 11α-hydroxyandrost-4-en-3,17-dione, was extracted into an aqueous phase with about half saturated sodium bicarbonate solution. The aqueous phase was washed with 1—1 ether-ethyl acetate to remove any starting material and the aqueous phase was acidified by dropwise addition of 6 N hydrochloric acid. Again the acid succinate was extracted with 1—1 ether-ethyl acetate, washed with water until neutral, dried over sodium sulfate, filtered and concentrated to dryness. (Note: This extraction process will be hereafter called the "acid succinate extraction procedure.") The residue was triturated with small amounts of ethyl acetate and recrystallized twice with one charcoal treatment from ethyl acetate-acetone to give 2.2 g. of the acid succinate.

| | |
|---|---|
| m.p. alc | 181–191° |
| $\lambda$max. 243 m$\mu$ $\epsilon=$ | 15,850 |
| Mol. wt. | 402 (M+ by Mass Spectrocopy) |
| I.R. | agreeable for proposed structures |
| NMR | agreeable for proposed structures |
| Anal. calcd. for | C, 68.63; H. 7.51 |
| Found | C, 68.49; H. 7.43 |

EXAMPLE 7

11α,17α-dihydroxypregn-4-en-3,20-dione 11-acid succinate

Using the procedure of Example 6, 6 g. of 11α,17α-dihydroxyprogesterone gave the acid succinate, 1.3 g., m.p. 215°–220°, in the first crop and 2.0 g. m.p. 214°–218° in the second crop from acetone-hexane; $\lambda$max.$^{alc}$243 m$\mu$ $\epsilon$=16,150. The IR and NMR spectra were both agreeable for the proposed structure.

Anal. Calcd. for C, 67.24; H. 7.67. Found: C, 67.17; H, 7.70.

EXAMPLE 8

11α-hydroxy-5α-pregnan-3,20-dione acid succinate

Following the procedure of Example 6 described above, 3 g. of 11α-hydroxypregnanedione was converted to 2.33 g. of its acid succinate, after recrystallization from methanol-water.

EXAMPLE 9

11α,17β-dihydroxy-7β,17α-dimethylandrost-4-en-3-one 11-acid succinate

This succinate was prepared by the procedure of Example 6 from 0.21 g. of 11α,17β-dihydroxy-7β,17α-dimethylandrost-4-en-3-one except the reaction mixture was more dilute and additional reflux time was required.

The product could not be purified by crystallization, so it (about 200 mg.) was streaked on an 8 × 8 preparative TLC plate and developed with 50—50—10 ethyl acetate-cyclohexane-acetic acid. The product was located under U.V. light, scraped off while the plate was still damp with solvent and eluted with ethyl acetate. The solvent was removed on the rotary evaporator and the residue was dissolved in ether and washed several times with water to remove the acetic acid. The ether solution was dried ($Na_2SO_4$) and concentrated to dryness. The product was crystallized from ether containing a drop of acetone. The yield was 80 mg.

EXAMPLE 10

11α,17β-dihydroxyandrost-4-en-3-one 11-acid succinate

Four grams of 11α-hydroxytestosterone, 6 g. of succinic anhydride and 50 ml. of pyridine was refluxed for 20 hours under nitrogen. It was worked up by the acid succinate extraction procedure to give 4.4 g. of a brown foam. By titration with 0.1N sodium hydroxide it contained two succinate groups and was the 11,17-disuccinate. To hydrolyze off the 17-succinate, 1.0 g. was dissolved in 9 ml. of 1.0N sodium hydroxide and diluted immediately with 90 ml. of water and purged with nitrogen. After 20 hours an aliquot was removed acidified, extracted and esterified with diazomethane. TLC showed no bis succinate. The major spots were the monosuccinate and some 11α-hydroxytestosterone.

The whole reaction was worked up by the acid succinate procedure described previously. A like 3.4 g. run was made, and the two runs were combined and the monosuccinate was recrystallized from acetone to give 1.1 g. of product, m.p. 200°–209° C. $\lambda$max.$^{alc}$ 243 nm, $\epsilon$=15,800; nmr ($CDCl_3$), $\delta$ 0.80 (C-18), 1.18 (C-19), 2.42 ($COCH_2$-$CH_2CO$).

EXAMPLE 11

11β-hydroxyestrone 11-acid succinate

The 3,11-bis acid succinate was prepared by the procedure of Example 10 from 1.0 g. of 11β-hydroxyestrone. The 3-succinate group was hydrolyzed by dissolving 1.0 g. in 50 ml. of water containing 10 g. of potassium carbonate. After keeping at room temperature for 16 hours the solution was acidified and the product isolated by the usual acid succinate extraction procedure. The product was purified by chromatography by the dissolving in acetone and pouring on a 70 g. dry silica gel column. The product was eluted with acetone containing 2% acetic acid and recrystallized to give 0.5 g. of 11β-hydroxyestrone 11-acid succinate.

Likewise 3,11α-dihydroxyestra-1,3,5(10)-trien-17-one is converted to 3,11α-dihydroxyestra-1,3,5(10)-trien-17-one 11-acid succinate.

EXAMPLE 12

1,3,5(10)estratrien-3,11β,17β-triol 11-acid succinate

A solution of 0.37 g. 11β-hydroxyestrone 11-acid succinate in 10 ml. of saturated aqueous sodium bicarbonate was cooled in an ice bath and 50 mg. of sodium borohydride was added. (TLC-Silica gel 45—55—10 ethyl acetate-cyclohexane-acetic acid). The product was isolated by the usual acid succinate procedure and recrystallized from tetrahydrofuran-water. The yield was 0.3 g. of 1,3,5(10)estratrien-3,11β,11β-triol 11-acid succinate.

Likewise 3,11α-dihydroxyestra-1,3,5(10)-trien-17-one 11-acid succinate is converted to estra-1,3(5,10)-triene-3,11α,17β-triol 11-acid succinate.

EXAMPLE 13

3β,11α-dihydroxyandrost-5-en-17-one 11-acid succinate

Five grams of 6β,11α-dihydroxy-3α,5α-cycloandrostan-17-one was converted to 6.8 g. of the bis acid succinate using the procedure of Example 10.

The bis acid succinate was dissolved in 340 ml. of acetone and 17 ml. of 1 N aqueous perchloric acid was added. After keeping at room temperature for 24 hours, it was worked up by the usual acid succinate extraction procedure. The product was recrystallized from acetone with charcoal treatment to give 3.55 g. of 3β,11α-dihydroxyandrost-5-en-17-one.

EXAMPLE 14 androst-5-ene-3β,11α,17β-triol 11-acid succinate

EXAMPLE 17

11α,21-dihydroxypregn-4-en-3,20-dione 11-acid succinate

The bis acid succinate was prepared by the procedure of Example 10 from 1.0 g. of 11α,21-dihydroxypregn-4-en-3,20-dione, and the hydrolysis of the 21-succinate group was also done in 0.1 N sodium hydroxide to yield 600 mg. of 11α,21-dihydroxypregn-4-en-3,20-dione 11-acid succinate amorphous product which resisted crystallization.

EXAMPLE 18

11α,20α-dihydroxypregn-4-en-3-one and
11α,20β-dihydroxypregn-4-en-3-one

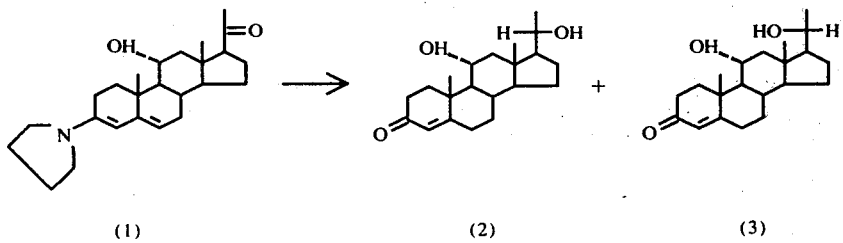

(1)    (2)    (3)

A solution of 1.5 g. of 3β,11α-dihydroxy-androst-5-en-17-one was dissolved in 40 ml. of saturated aqueous sodium bicarbonate, 20 ml. of water and 10 ml. of 95% alcohol, cooled in an ice bath and 200 mg. of sodium borohydride was added. The mixture was worked up by the usual acid succinate extraction procedure and the product was recrystallized from acetone-SSB to give 1.28 g. of androst-5-ene-3β,11α,17β-triol 11-acid succinate.

EXAMPLE 15

11α,17β-dihydroxy-5α-androstan-3-one 11-acid succinate

The bis acid succinate was prepared from 6 g. of 11α-hydroxy-5α-dihydrotestosterone by the procedure of Example 10. It (6.73 g.) was hydrolyzed in 532 ml. of .1 N sodium hydroxide. After recrystallization from acetone-hexane 3.55 g. of 11α,17α-dihydroxy-5α-androstan-3-one 11-acid succinate was obtained.

EXAMPLE 16

5α-androstan-3β,11α,17β-triol 11-acid succinate

To a cold (5° C.) solution of 0.5 g. of 11α-hydroxy-dihydrotestosterone 11-acid succinate in 13.3 ml. of aqueous saturated sodium bicarbonate, 6.65 ml. water and 3.33 ml. 95% ethyl alcohol was added 66.5 mg. of sodium borohydride. After 5 minutes TLC silica gel plate developed in 3% acetic acid, 40% EtOAc and 57% cyclohexane showed the reaction was complete. 6 N HCl was added dropwise with stirring and cooling until reaction just turned acidic. The product was extracted with ethylacetate and washed several times with water, dried over sodium sulfate, filtered and concentrated to dryness. It was chromatographed through acid washed silica gel to remove some very polar impurity. The fractions containing the product were combined and concentrated to give 5α-androstan-3β,11α,17β-triol 11-acid succinate a solid glassy foam residue which resisted crystallization, 0.15 g.

A 19.3 g. sample of (1) was heated under reflux for 1 hour with 4 g. of lithium aluminum hydride in 1000 ml. of 1:1 benzene-ether. The mixture was cooled to 0°; ethyl acetate (20 ml.) and water (20 ml.) were added cautiously and the mixture was filtered. The filtrate was heated with 40 ml. of acetic acid in 120 ml. of methanol and 200 ml. of 15% aqueous sodium hydroxide and stirred vigorously for 15 minutes at room temperature. The organic layer was washed with aqueous hydrochloric acid, water, aqueous potassium bicarbonate and dried to give 14.75 g. of the mixture of alcohol as a white foam.

The mixture was chromatographed on 1 kg. of silica gel packed in 49:1 methylene chloride:methanol and eluted with 1.5 liter portions of the same solvent mixture. Fractions 12–16 contained 2.92 g. of 20α-isomer which was crystallized from acetone-hexanes and aqueous methanol to give 2.13 g. (12.8%) of (2), m.p. 197°–201°. Fractions 17–20 contained mixtures. Continued elution with 19:1 methylene chloride-methanol give 9 g. of the 20β-isomer in fractions 22–25. Crystallization as described for the 20α-isomer give 5.26 g. (31.6%) of (3), m.p. 174°–177.5°.

Anal. Calcd. for $C_{21}H_{32}O_3$ (332.47): C, 75.86; H, 9.70. Found: C, 75.23; H, 9.78. $[\alpha]_D + 87°$ (C 0.813 $CHCl_3$) IR (Cm$^{-1}$): 3360, 3320, 1670, 1660, 1615, 1345, 1300, 1270, 1235, 1190, 1110, 1085, 1065, 1035, 945, 880, 865. NMR ($CHCl_3$), δ): $C_{18}$ (0.73), $C_{21}$ (1.23, J=6, $C_{19}$ (1.31).

EXAMPLE 18a

11α,20α-dihydroxypregn-4-en-3-one 11-acid succinate

The 11,21-bis acid succinate (2.5 g.) was prepared from 11α,20α-dihydroxypregn-4-en-3-one (1.97 g.) by the procedure of Example 10. It was dissolved in 150 ml. of 0.1 N sodium hydroxide. After 17 hours an aliquot was analyzed by TLC after converting it to its methyl esters. The bis acid succinate was the most intense spot. Another 30 ml. of 0.1 N sodium hydroxide was added and after another 25 hours TLC analysis of the methyl esters showed considerably 11-monosuccinate, some bis succinate and some 11,20-diol. The solution was stored in the refrigerator for 2 more days and worked up by the usual acid succinate extraction procedure. TLC still showed some bis acid succinate. The product, 1.9 g. was dissolved in 50—50—5 ethyl acetate-cyclohexane-acetic acid and a little methylene chloride and chromatographed on a 200 g. of Woelm Grade III alumina column by the dry column technique.

The zone containing the product was cut out and eluted with 100—5 ethyl acetate-acetic acid. The eluate was concentrated to remove the ethyl acetate. The residue was dissolved in ether and washed with water to remove the acetic acid. The ether was dried and concentrated and the residue was recrystallized from ether to give 0.55 g. of 11α,20α-dihydroxypregn-4-en-3-one 11-acid succinate.

EXAMPLE 19

11α,17β-dihydroxy-7β,17-dimethylandrost-4-en-3-one 11-acid succinate

The crude product from the bioconversion of 2.7 g. of 7β,17α-dimethyltestosterone with *Sporotrichum sulfurescens* was dissolved in methylene chloride, slurried with 50 g. silica gel and poured onto a 250 g. silica gel chromatogram column. The product was eluted by gradient between 5 liters 30% ethyl acetate-SSB and 5 liters 80% ethyl acetate-hexane then with 2 liters 80% ethyl acetate-hexane and collected in 400 ml. fraction. Fractions 25–31 containing the product were combined and recrystallized twice from acetone-hexane to give 250 mg. of 11α-hydroxylated product, m.p. 195°–203° C; U.V. $\lambda max.^{alc} 244$ nm $\epsilon = 15,150$; ir (mull) 3410 sh, 3370 (OH) 1675 sh, 1655, 1650 (C=O) 1610 (C=C); m.s. m/e 332, 317, 314, 299; nmr (CDCl$_3$) δ 0.9 (s, C-18), 1.09 (m, C-7), 1.2 (s, C-19) 1.3 (s, C-17), 4.0 (m, C-11), 5.69 (s, C-4).

Anal. Calcd. for C$_{21}$H$_{32}$O$_3$ (332.47): C, 75.86; H, 9.70. Found: C, 75.47; H, 9.96.

Following the procedure of Example 1 but substituting 11α,17β-dihydroxy-7β,17-dimethylandrost-4-en-3-one for 11α-hydroxyprogesterone, there is obtained 11α,17β-dihydroxy-7β,17-dimethylandrost-4-en-3-one 11-acid succinate. It was purified by preparative thin layer chromatography on a silica gel plate in a 5—5—1 ethyl acetate-cyclohexan-acetic acid system.

EXAMPLE 20

Preparation of conjugates with tyrosine methyl ester (11α-hydroxyprogesterone 11-ester with methyl-N-(3-carboxypropionyl)-2-tyrosinate ester)

To a solution of 1.0 g. of 11α-hydroxyprogesterone acid succinate in 5 ml. of tetrahydrofuran (purified by percolating through alumina) was added 0.405 g. of carbonyldiimidazole under N$_2$ and careful exclusion of moisture. After 30 minutes, 0.49 g. of L-tyrosine methyl ester was added to the clear yellow solution. The solution was stored 20 hours and part of the solvent was evaporated with a stream of N$_2$ then diluted with ethyl acetate. The ethyl acetate solution was washed with dilute hydrochloric acid water and sodium bicarbonate solution, dried over MgSO$_4$, filtered and concentrated to dryness. The crude product was chromatographed on a 100 g. silica gel column packed wet with hexane and eluted by gradient between 5 liters of 20% ethyl acetate-hexane and 5 liters of 80% ethyl acetate-hexane. Fractions (400 ml. each) no. 20–24 contained the amide. These fractions were combined in acetone, filtered to remove the dust and concentrated to a light yellow glassy foam: $\lambda max.^{alc}$ 242 nm $\epsilon = 14,500$.

The nmr bands which characterize the succinyl tyrosine amide methyl ester are listed below. NMR (DMSO d-6) δ 2.39 (S, COCH$_2$-CH$_2$-CO) 3.82 (d, J=7, CH-CH$_2$-O-OH), 3.55 (S, OCH$_3$), 4.38 (q, J=6-7,

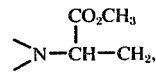

5.05 (m, C-11), 6.60, 7.00 (pair of d, J=8,

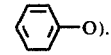

In like manner other steroid 11-hemisuccinates described above are converted to their conjugates with d, 1, or d,1-tyrosine methyl ester. Other esters of tyrosine also can be used, e.g., ethyl, propyl, cyclohexyl, benzyl, etc.

EXAMPLE 21

Preparation of conjugates with tyrosine methyl ester (11α-hydroxyprogesterone 11-ester with methyl-N-(3-carboxypropionyl)-2-tyrosinate)

To a solution of 100 ml. of 11α-hydroxypregn-4-ene-3,20-dione acid succinate and 100 mg. of 1-tyrosine methyl ester in 5 ml. of dioxany was added a solution of 45 mg. of 1-ethyl-3-(3-dimethylaminopropyl)carbodiimide hydrochloride in 10 drops of water. After standing at room temperature for 20 hours water was added and the product was extracted with ethyl acetate. The extract was washed with aqueous sodium bicarbonate solution, dilute hydrochloric acid and water and dried of magnesium sulfate. This solvent was evaporated leaving a residue of 11α-hydroxyprogesterone 11-ester

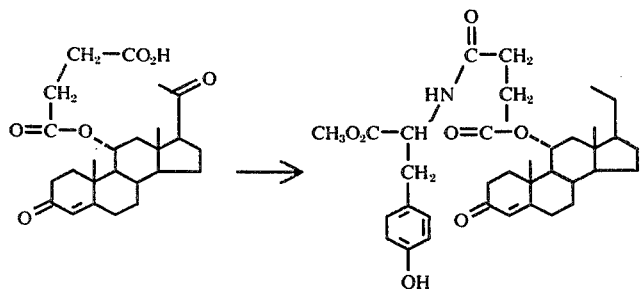

with methyl-N-(3-carboxypropionyl)-2-tyrosinate.

In like manner other steroid 11-hemisuccinates described above are converted to their conjugates with d, l, or d, l-tyrosine methyl ester. Other esters of tyrosine can also be used, e.g., ethyl, propyl, cyclohexyl, benzyl, etc.

EXAMPLE 22

To a solution of 100 mg. of 11α-hydroxyprogesterone 11-acid succinate and 100 mg. of tyrosine methyl ester in 5 ml. of dioxane was added 45 mg. of 1-ethyl-3(3-dimethylaminopropyl)carbodiimide hydrochloride in 10 drops of water dropwise. The solution which was monitored by thin layer chromatography, was allowed to stand overnight at room temperature, was diluted with water and extracted with ethyl acetate. The extract was washed with dilute bicarbonate, dilute hydrochloric acid and with water. The extract was dried with magnesium sulfate and evaporated to give 11α-hydroxyprogesterone 11-ester with methyl-N-(3-carboxypropionyl)-2-tyrosinate ester.

In like manner, but substituting in examples 21 and 22 above the following: The 11-acid succinates of
1. 11α,20α-dihydroxypregn-4-en-3-one,
2. 11α,17α-dihydroxyprogesterone,
3. 11α,17β-dihydroxyandrost-4-en-3-one,
4. 11α,17β-dihydroxy-5α-androsta-3-one,
5. 11α-hydroxyestrone,
6. 11α-hydroxyestradiol,
7. 11β-hydroxyestrone,
8. 11β-hydroxyestradiol,
9. 3β,11α-dihydroxyandrost-5-en-17-one,
10. androst-5-ene-3β,11α,17β-triol,
11. 11α-hydroxypregnenolone, and
12. 11α,17α-dihydroxypregnenolone, there are produced:

1. 11α,20α-dihydroxypregn-4-en-3-one 11-ester with methyl-N-(3-carboxypropionyl)-2-tyrosinate,
2. 11α,17α-dihydroxyprogesterone 11-ester with methyl-N-(3-carboxypropionyl)-2-tyrosinate,
3. 11α,17β-dihydroxyandrost-4-en-3-one 11-ester with methyl-N-(3-carboxypropionyl)-2-tyrosinate,
4. 11α,17β-dihydroxy-5α-androsta-3-one 11-ester with methyl-N-(3-carboxypropionyl)-2-tyrosinate,
5. 11α-hydroxyestrone 11-ester with methyl-N-(3-carboxypropionyl)-2-tyrosinate,
6. 11α-hydroxyestradiol 11-ester with methyl-N-(3-carboxypropionyl)-2-tyrosinate,
7. 11β-hydroxyestrone 11-ester with methyl-N-(3-carboxypropionyl)-2-tyrosinate,
8. 11β-hydroxyestradiol 11-ester with methyl-N-(3-carboxypropionyl)-2-tyrosinate,
9. 3β,11α-dihydroxyandrost-5-en-17-one 11-ester with methyl-N-(3-carboxypropionyl)-2-tyrosinate,
10. androst-5-ene-3β,11α,17β-triol 11-ester with methyl-N-(3-carboxypropionyl)-2-tyrosinate,
11. 11α-hydroxypregnenolone 11-ester with methyl-N-(3-carboxypropionyl)-2-tyrosinate, and
12. 11α,17α-dihydroxpregnenolone 11-ester with methyl-N-(3-carboxypropionyl)-2-tyrosinate.

We claim:
1. A compound having the following structural formula

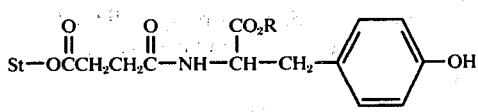

wherein St is a steroid moiety linked through the 11-carbon atom and selected from the group consisting of those moieties corresponding to 20α-hydroxypregn-4-en-3-one
20β-hydroxypregn-4-en-3-one
17α-hydroxypregn-4-ene-3,20-dione
21-hydroxypregn-4-ene-3,20-dione
17α,21-dihydroxypregn-4-ene-3,20-dione
17β-hydroxyandrost-4-en-3-one (testosterone)
17β-hydroxy-5α-androstan-3-one
17β-hydroxy-5β-androstan-3-one
5α-androstane-3β,17β-diol
17β-hydroxyestr-4-en-3-one (19-nortestosterone)
estrone
estradiol
estriol
estr-5-ene-3β,17β-diol
androst-5-ene-3β,17β-diol
dehydroepiandrosterone
pregnenolone
21-hydroxypregnenolone
17α-hydroxypregnenolone
17,21-dihydroxypregnenolone
17β,17α-dimethyl-17-hydroxyandrost-4-en-3-one, and R is a lower alkyl group containing from 1 to 6 carbon atoms inclusive.

* * * * *